(12) United States Patent
De Keizer

(10) Patent No.: US 10,060,092 B2
(45) Date of Patent: Aug. 28, 2018

(54) MEASUREMENT DEVICE FOR PERFORMING MEASUREMENT ON A MIXTURE OF WATER AND COLLECTED MATERIAL

(71) Applicant: IHC Systems B.V., Sliedrecht (NL)

(72) Inventor: Cornelis De Keizer, Dordrecht (NL)

(73) Assignee: IHC Holland IE B.V., Sliedrecht (NL)

( * ) Notice: Subject to any disclaimer, the term of this patent is extended or adjusted under 35 U.S.C. 154(b) by 197 days.

(21) Appl. No.: 14/781,013

(22) PCT Filed: Mar. 28, 2014

(86) PCT No.: PCT/NL2014/050193
§ 371 (c)(1),
(2) Date: Sep. 28, 2015

(87) PCT Pub. No.: WO2014/158024
PCT Pub. Date: Oct. 2, 2014

(65) Prior Publication Data
US 2016/0053461 A1    Feb. 25, 2016

(30) Foreign Application Priority Data

Mar. 28, 2013 (NL) ........................... 2010538

(51) Int. Cl.
*E02F 3/90* (2006.01)
*G01N 15/02* (2006.01)
(Continued)

(52) U.S. Cl.
CPC ......... *E02F 3/907* (2013.01); *G01N 15/0227* (2013.01); *G01N 15/04* (2013.01);
(Continued)

(58) Field of Classification Search
CPC ..... E02F 3/907; G01N 15/0227; G01N 15/04; G01N 33/24; G01N 2015/0053; H04N 5/235; H04N 5/2628; G06T 7/0004
See application file for complete search history.

(56) References Cited

U.S. PATENT DOCUMENTS 3,926,050 A * 12/1975 Turner .................... E02F 3/907
                                                     73/438
4,444,229 A *  4/1984 Beck ..................... B01D 21/26
                                                      141/1
(Continued)

FOREIGN PATENT DOCUMENTS

GB       2371858 A  *  8/2002  ......... G01N 15/0227
KR   1020120074772        7/2012
(Continued)

OTHER PUBLICATIONS

International Search Report dated Jun. 27, 2014 for corresponding PCT Application No. PCT/NL2014/050193, 3 pages.
(Continued)

*Primary Examiner* — Jamie L McGowan
(74) *Attorney, Agent, or Firm* — NLO N.V.; Catherine A. Shultz; Lindsey A. Auerbach

(57) ABSTRACT

A measurement device for performing measurements on a mixture of water and collected material includes a pipe section through which the mixture can be guided. The pipe section includes a window. The measurement device further includes an image capturing device arranged to capture an image of the collected material through the window. The image can be used to determine a grain size distribution of the collected material, which can be used to optimize the collecting process.

17 Claims, 3 Drawing Sheets

(51) Int. Cl.
*G01N 15/04* (2006.01)
*G01N 33/24* (2006.01)
*G06T 7/00* (2017.01)
*H04N 5/235* (2006.01)
*H04N 5/262* (2006.01)
*G01N 15/00* (2006.01)

(52) U.S. Cl.
CPC .......... *G01N 33/24* (2013.01); *G06T 7/0004* (2013.01); *H04N 5/235* (2013.01); *H04N 5/2628* (2013.01); *G01N 2015/0053* (2013.01)

(56) References Cited

U.S. PATENT DOCUMENTS

| | | | | |
|---|---|---|---|---|
| 5,172,497 | A * | 12/1992 | Lemonds | E02F 3/907 37/308 |
| 5,815,264 | A * | 9/1998 | Reed | G01N 21/53 250/574 |
| 6,122,956 | A * | 9/2000 | Klausner | G01N 27/06 324/439 |
| 7,162,057 | B1 * | 1/2007 | Roth | G01N 15/0227 137/13 |
| 2002/0133982 | A1 * | 9/2002 | Price | E02F 3/8858 37/307 |
| 2008/0282583 | A1 * | 11/2008 | Koellner | E02F 3/304 37/348 |

FOREIGN PATENT DOCUMENTS

| | | |
|---|---|---|
| WO | 2011080216 A1 | 7/2011 |
| WO | 2012039608 A9 | 3/2012 |
| WO | 2014014350 A1 | 1/2014 |
| WO | 2014158024 A1 | 10/2014 |

OTHER PUBLICATIONS

Focus Industry, Ermittlung der Fordermasse auch unter Extrembedingungen, 2010, 2 pages.

D. Carlson, Nucleonics—and how they are employed for non-contacting process measurement, Apr. 1978, 5 pages.

A. Hadjidakis, Automatisering Van Een Sleephopperzuiger, 6 pages.

I.H.C. Holland, Instrumentatie Van Moderne Sleepzuigers, 7 pages.

Marquardt, Optimization of Sand and Gravel Extraction on a Dredger with Fully Automatic Online Particle Size Analysis, 2000. 6 pages.

N.P. McManus, Automatic Dredging Controls Designed for Hopper Dredges, Jul. 1975, 3 pages.

* cited by examiner

MEASUREMENT DEVICE FOR PERFORMING MEASUREMENT ON A MIXTURE OF WATER AND COLLECTED MATERIAL

FIELD OF THE INVENTION

The present invention relates to a measurement device for performing measurements on a mixture of water and collected material. The invention further relates to a method of transporting a mixture of water and collected material.

BACKGROUND

Vessels for collecting material from an underwater bottom are known.

Examples of such vessels are dredging vessels, such as trailing suction hopper dredgers, cutter suction dredgers. Dredging vessels are used to maintain the depth of or deepen shipping channels, to dredge new shipping channels, and for sand and gravel extraction, for example for infrastructure projects and land reclamation.

Another example are a mining vessels, which are used to collect mining material from the underwater bottom. The mined material may comprise minerals, hydrates, diamonds, gold, copper, manganese, nickel, zinc.

The term collected material used in this text therefore refers to both dredged material and mined material. The collected material comprises a plurality of grains.

The collected material may be loaded into a loading space (hopper) or may be discharged via a discharge pipe line to a remote location.

On hopper dredgers the dredged material, also referred to as soil, is pumped into the loading space of the dredging vessel. In order to do this, the dredged material is mixed with water, creating a slurry, which can be pumped. When the slurry is in the loading space, the dredged material will settle.

The determination of the settling speed of the dredged material in the loading space of the dredging vessel is an important parameter for ensuring that the dredging is as efficient as possible. This also applies to mined materials which are stored in a loading space or processed by a concentration plant.

Depending on the type of work, widely differing materials are dredged or mined, which may have different typical sizes: sludge, clay, fine sand, coarse sand, gravel, rock, minerals, hydrates and often a combination thereof. The settling speed of the material depends on the grain size of the collected material.

The speed with which the loading space is filled and the ratio between the amount of water and dredged material in the slurry preferably matches the settling speed of the collected material to make the dredging or mining process as efficient as possible.

If the loading space is filled too quickly, a part of the collected material will not be given enough time to settle and will leave the ship once more via an overflow. Filling which is too slow is not attractive from a cost perspective. It is therefore very important to know how quickly the collected material settles.

To allow the loading process to run as efficiently as possible, it is necessary to know the settling speed: sludge does not settle, fine sand settles very slowly, coarse sand more quickly, whereas gravel and rock drop immediately. Depending on this settling speed and the associated speed at which the height of the settled bed rises, the dredging or mining process can be devised differently in terms of loading speed and density of the slurry, so that the settling process will run more efficiently.

Other types of operations, such as oil extraction operations, employ various methods for analysis of suspended fine particles in a fluid flow. For example, in WO2011/080216, a measuring unit is used that uses a camera with a light source for sampling images of a hydrocarbon fluid flow. The images are sent to an electronics unit for analyzing and measuring the very small suspended particles, such as oil droplet and solid particle concentrations separately to determine whether the fluid may cause damage due to excessive oil or solids droplet content. However, for mining or dredging operations, the particles are typically larger, meaning that they will settle and will affect flows during the process.

Different methods are known to optimize the dredging or mining process. For instance, the height of the settled bed can be monitored during dredging via radioactive means, or indirectly calculated by pressure measurements. Information about the determined height of the settled bed and the increase of the determined height can be used to control the dredging or mining process. Also, information about the average grain size of the collected material can be derived. One such way to derive this is disclosed in the article "Optimization of Sand and Gravel Extraction on a Dredger with Fully Automatic Online Particle Size Analysis." For this, a sample is taken from the dredge, and particles from the sample are dried, put on a belt and then dropped off the belt. While the particles are free-falling, photos are taken and then analyzed.

However, such methods require relatively complicated and vulnerable sensor equipment and require separation and/or drying out the particles from the slurry. Also, such methods only provide information about an average grain size. Furthermore, as the increase of the settled bed is a relatively slow process and the other processes for analyzing require taking out a sample, drying and then analyzing; information about the average grain size is only available with a certain delay, typically in the order of 5-10 minutes. Consequently, adjusting the dredging or mining process can only be done with a delay.

In case the mixture of water and collected material is to be discharged via a discharge pipe line, for instance from a loading space or directly after it has been collected, detailed information about the grain size of the collected material is also advantageous, as this information can be used to determine an appropriate discharge flow speed, in which settling of the collected material inside the discharge pipe line is prevented or at least minimized. This aspect is important in both dredging and mining.

SUMMARY

One object is to provide a method and a device for obtaining more detailed information about the grain size of collected material, i.e. material collected from an underwater bottom such a dredged or mined material. An other object is to provide a method and a device for obtaining information about the grain size of the collected material more quickly.

This object is achieved by a measurement device for performing measurements on a mixture of water and collected material, the measurement device comprising a pipe section through which the mixture can be guided, the pipe section comprises a window, and the measurement device comprises an image capturing device arranged to capture an image of the collected material through the window.

Collected material may be dredged material or mined material. The material collected from an underwater bottom is transported through a pipe towards the loading space of a vessel and/or the mixture is discharged via a discharge pipe line. Discharge may take place directly or may take place from a loading space.

The pipe section may be part of a collecting pipe for collecting material from an underwater bottom, but may also be part of a discharge pipe line for discharging the mixture. The pipe section may be positioned upstream of downstream of a pump for transporting the mixture through the pipe section.

In a pipe section a window is mounted and through this window images of the passing (soil) grains are taken. The window is translucent for at least a wavelength used by the image capturing device.

The image capturing device may be an analogue or digital video or photo camera and is positioned outside the pipe section.

Such a measurement device has the advantage that information can be obtained about the dredged material, in particular about the grain size, such as for instance about the average grain size or about the grain size distribution. This information is available relatively quickly, for instance within seconds, as the information can easily be retrieved from the image by appropriate image processing and recognition techniques. Also, this information can be determined and updated constantly during dredging.

Control signals to control dredging or mining equipment may be based on such information, as will be discussed in more detail below.

According to an embodiment the measurement device comprises a control unit arranged to receive an image captured by the image capturing device and analyse the image to determine information about the collected material, such as about an average grain size and a grain size distribution of the dredged material.

The term grain size is used here to refer to all sorts of measures that may be used to reflect information about the grain size, such as radius, diameter, perimeter.

Grain sizes can be determined by analyzing captured images using appropriate processing techniques. An average grain size may be computed relatively quickly, allowing to control the dredging process in response to the determined average grain size.

Instead of determining an averaged grain size, information about a grain size distribution of the dredged material may now be determined. This information may for instance comprise an average grain size and a standard deviation of the grain size or any other suitable statistical parameter(s).

By determining (information about) a grain size distribution, the dredging or mining process can be controlled to be more efficient.

For instance, in case of dredging process, if only an average grain size is computed, the operator or software may decide to set the dredging speed at a moderate speed to allow the grains to settle and reduce the amount of grains leaving via the overflow. However, if a grain size distribution is known showing that the mixture comprises grains too small to settle within a reasonable time and further comprises grains big enough to settle very quickly, the dredging speed may be set at a higher speed, as the small grains will leave via the overflow anyway and the big grains will settle anyway.

The measurement device, in particular the control unit, may be arranged to generate control signals to control operating parameters of dredging or mining equipment. The information about a grain size distribution of the dredged material may also comprise a plurality of ranges of sizes, including an indication of the amount of grains falling within these ranges. In the dredging industry this is done according to the British Standard 1377 (dry sieving). The soil is sieved by using a mechanical sieve apparatus. The distribution may for instance look as follows:

| Particle size [μm] (sieve diameter) | Percentage on sieve [%] |
|---|---|
| 4000 | 0.0 |
| 2800 | 0.0 |
| 2000 | 16.4 |
| 1400 | 10.6 |
| 1000 | 10.2 |
| 710 | 10.0 |
| 500 | 8.2 |
| 355 | 9.9 |
| 250 | 14.3 |
| 180 | 12.6 |
| 125 | 5.3 |
| 90 | 1.2 |
| 75 | 0.3 |
| 63 | 0.9 |
| 45 | 0.1 |
| 38 | 0.0 |

The information about a grain size distribution of the dredged material may also be in the form of a formulae, such as a polynomial.

According to an embodiment the control unit is arranged to analyse the image to determine information about at least one of the average grain size and the grain size distribution of the collected material using image recognition techniques. The control unit may determine information about a plurality of grains in the image and compute an average or grain size distribution from this. The control unit may also determine information about a plurality of grains in a plurality of captured images and compute a single grain size distribution based on the information from the plurality of images.

According to an embodiment the measurement device comprises a light source, for instance a flash light, arranged to generate a light beam to light at least part of the slurry in the image of the image capturing device.

The light source may be a LED light. Also, by using the light source in a flash mode, a relatively high power can be applied to the light source, without the risk of overheating the light source.

According to an embodiment the lights source is ring-shaped light source positioned concentrically with respect to a viewing direction of the image capturing device. The ring-shaped light source may be positioned around the image capturing device such that light emitted enters the window.

The ring-shaped light source may be a LED-ring, i.e. a plurality of LED's positioned in a ring configuration.

The ring-shaped light source may have a diameter of 50 mm.

The ring-shaped light source may have a diameter that is substantially equal (within 15%) to the dimension of the window. In case the window is round, the diameter of the ring-shaped light source may be substantially equal to the diameter of the window.

The image capturing device may comprise a lens. The lens may have a diameter of approximately 16 mm.

According to an embodiment the measurement device comprising a density measurement device for measuring a density of the mixture.

Density measurement devices are known, such as a density measurement device arranged to radiate a radio-active or electromagnetic radiation through a pipe section and a density can be determined by measuring the amount of radiation penetrating the pipe section. Alternative density measurement devices are based on weighing a pipe section, as the weight depends on the density of the mixture.

The density measurement device may be used to determine whether or not dredged material is passing. If the density of the mixture is larger than water, but no (or very few) grains are detected by the image capturing device, then one knows that very fine dredged material is passing; that means material with a grain size smaller than the video image resolution (e.g. 50 or 100 µm).

Control signals to control dredging or mining equipment may be based on such information.

The measured density may also be used to estimate the occurrence of overlapping grains. If the density is relatively high, the determined (information of) grain size distribution may be corrected to take into account the fact that some grain sizes are incorrect as grains may be overlapping in a captured image, which may result in smaller grains not being detected or being measured as smaller than they actually are.

According to an embodiment the image capturing device is arranged to capture an image which has a movement blur of less than 100 µm, preferably less than 50 µm.

Grains smaller than approximately 100 µm will not settle, at least not within a period of time relevant for dredging processes. So, movement blur in the range of 50 µm-100 µm is acceptable, as there is no added value in determining a detailed grain size distribution below 100 µm as all grains smaller than 100 µm will behave similar, i.e. will not settle.

According to an embodiment the image capturing device is arranged to capture an image with a shutter time of 0.00001s or less.

The mixture will typically have a velocity of 10 m/s in the radial middle of the pipe section, and a velocity of 5 m/s close to the wall of the pipe section. Choosing a shutter time of 0.00001s will thus result in a movement blur of 100 µm in the middle of the pipe section and a movement blur of 50 µm close to the wall of the pipe section. Advantageously, the images are captured relatively close to the wall of the pipe section, so a blur of 50 µm or less is acceptable.

According to an embodiment the window is arranged to withstand a pressure difference of 30 bar, preferably 35 bar, between an inside of the pipe section and an outside of the pipe section.

As the pressure of the dredged material may be 36 bar, the window should be strong enough to withstand such pressures. The window may therefore be relatively thick, for instance has a thickness of at least 50% of its lateral dimensions. The window may for instance be round having a diameter of 50 mm or 25 mm and having a thickness of 16 mm or more.

According to an embodiment the image capture device is arranged to capture images in black and white.

This allows to capture images with a relatively high sensitivity with respect to colour images. That means that with black and white images less light is required and/or shorter shutter times (for sharper images) can be used.

According to an embodiment the image capturing device is set to capture an image with a focusing area positioned at a distance behind the window, the distance being in the range of 1-5 mm. Higher distances are difficult to achieve as the grain density is too high to look further into the mixture.

A diaphragm may be used to realise a desired Depth of Field (DOF). The DOF may typically be in the range of 3-5 mm, in particular 4 mm, where the image distance of interest is 1-5 mm behind the window.

According to an embodiment wherein the control unit (22) is arranged to generate control signals to control at least one of a pump, a visor (33), a water flap (34), a hoisting device, a water valve or swing winches based on one or more captured images of the collected material, for instance in dependence on determined information about the collected material.

In case of a cutter dredger, the control signals may in particular directed to a pump, water valve, hoisting winch, swing winches. In case of a trailing suction hopper dredger a hoisting winch may be added to this list.

The pump may be a collecting pump or a discharge pump. In case the measurement device is employed in a dredging process, the pump may be a collecting pump. The dredging equipment may comprise a drag head comprising a visor and possibly a water flap which can be controlled. The position of the suction tube to which the drag head is attached can be controlled by a hoisting device.

The dredging equipment may also be a cutter dredger, in which case at least the collecting pump, a water valve in a collecting pipe, a hoisting device and swing winches can be controlled.

According to an aspect there is provided a vessel, such as a dredging vessel or a mining vessel, comprising a measurement device as described above. The dredging vessel may for instance be a trailing suction hopper dredger or a cutter suction dredger.

According to an aspect there is provided a vessel for collecting material from an underwater bottom, the vessel comprising a collecting pipe which has a free end, which free end can be lowered to an underwater position, the vessel comprising a collecting device located at or in the vicinity of the collecting pipe, the vessel further comprising a pump, wherein the collecting pipe comprises a pipe section, the pipe section comprising a window, and the measurement device comprises an image capturing device arranged to capture an image of the collected material through the window.

The device may be a drag head, a cutter or a mining tool. The collecting pipe can be lowered by a hoisting device.

According to an embodiment the vessel comprises a discharge pump for discharging the mixture via a discharge pipe line, the discharge pipe line comprising a pipe section, the pipe section comprising a window, and the measurement device comprises an image capturing device arranged to capture an image of the collected material through the window.

The pump for collecting and discharging may be one and the same pump or may be separate pumps.

According to an embodiment the dredging vessel comprises a control unit arranged to receive and analyse at least one image captured by the image capturing device and generate control signals to control at least one of a collecting pump, a discharge pump, a visor, a water flap, a hoisting device, a water valve or one or more swing winches in dependence on the at least one captured image, in particular in dependence of determined information about one of an average grain size and a grain size distribution of the collected material.

This allows to quickly control and optimize the dredging process in response to the information obtained from the images. Instead of the average grain size and/or a grain size distribution of the collected material, other information relating to the grain size may be used as well to generate control signals.

According to an aspect there is provided a mining vessel comprising a measurement device as described above.

According to an aspect there is provided a method of transporting a mixture of water and collected material, wherein the method comprises:
  operating a pump to pump the mixture through a pipe,
  capturing at least one image of the collected material flowing through the pipe and analyzing the at least one image,
  controlling at least one of the ratio of water and collected material in the mixture and the operating speed of the pump based on the captured image.

The pump may be a collecting pump or a discharge pump. The pipe may be a collecting pipe or a discharge pipe line or may be in fluid communication with one of those.

Controlling the operating speed of the pump may be advantageous when collecting material to optimize the collecting process.

Controlling the operating speed of the pump may be advantageous to prevent or at least minimize settling of collected material inside the pipe line and/or prevent or at least minimize excessive wear of an inside of the (discharge) pipe line. This may in particular be advantageous in case the material is to be discharged via a discharge pipe line to a remote location, for instance from a mining or dredging vessel to the shore.

According to an embodiment the method is part of a dredging or mining process, the method comprises:
  collecting material from an underwater bottom or from loading space by loosening material from the underwater bottom or from the loading space and mixing the material with water creating the mixture of water and collected material.

According to an embodiment analyzing the at least one image comprises determining information about at least one of an average grain size and a grain size distribution of the collected material.

According to an embodiment controlling the ratio of water and collected material in the mixture can be done by one or more of
  controlling a rotational speed of the pump,
  controlling a position of a visor provided on a drag head of a trailing suction hopper dredger,
  controlling a water flap provided on the drag head of a trailing suction hopper dredger,
  controlling a depth of the excavation tool by a hoisting device,
  controlling a water valve provided on the collecting pipe of a cutter dredger and
  controlling a swing speed of a cutter dredger by swing winches.

The drag head may be used for collecting material from an underwater bottom. The excavation tool may be a drag head but may also be a cutter.

BRIEF DESCRIPTION OF THE DRAWINGS

Embodiments of the invention will be described below, purely by way of example, with reference to the accompanying schematic drawings, wherein corresponding components are indicated by corresponding reference symbols, and wherein.

The drawings are intended for illustrative purposes only, and do not serve to restrict the scope of protection, which is defined by the claims.

DETAILED DESCRIPTION

Embodiments will be discussed with reference to the figures.

Figure 1:
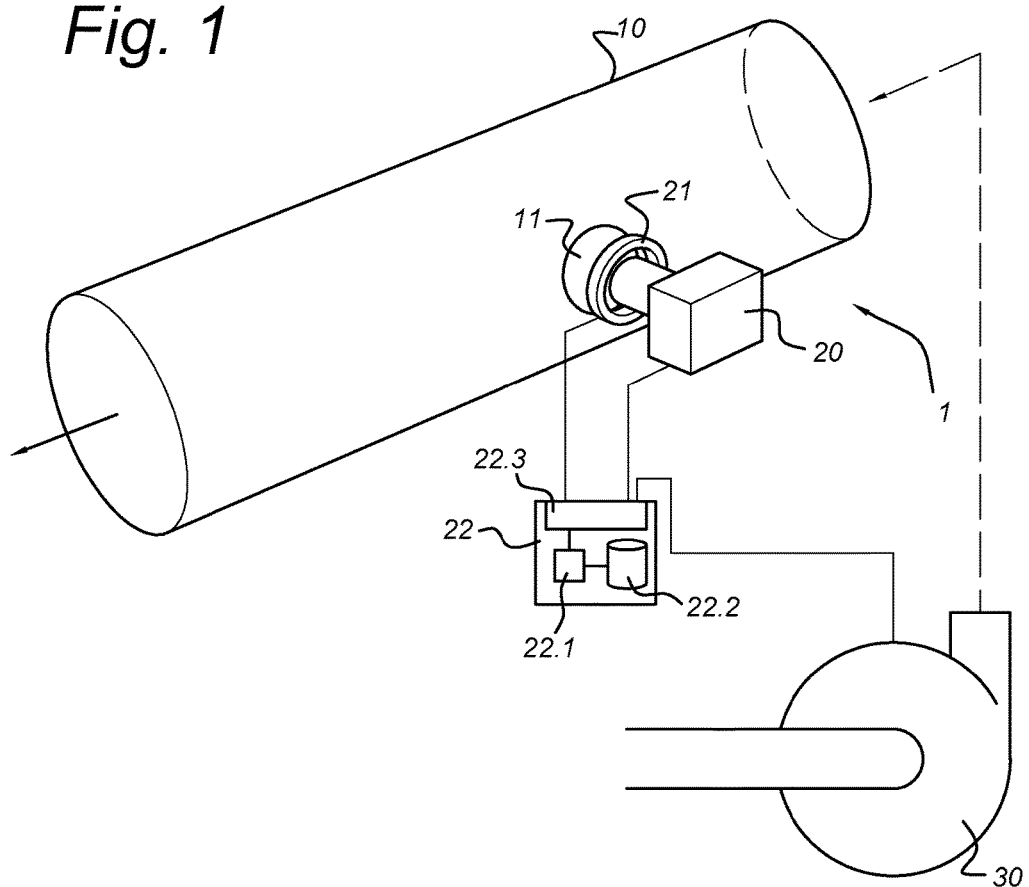
FIG. 1 schematically shows an embodiment of a measurement device according to an embodiment.

FIG. 1 schematically shows a measurement device 1 for performing measurements of grain sizes present in a mixture of water and dredged material flowing through a pipe section 10.

The pipe section 10 may be part of a collecting pipe used to pump the mixture from an underwater bottom to a loading space. The pipe section 10 may also be part of a discharge pipe line for discharging a mixture of water and collected material. The pipe section 10 may also be a relatively small side branch of the collecting pipe or discharge pipe.

The pipe section 10 comprises a window 11. The window may be round having a diameter of 50 mm. The window may be translucent to light and have a thickness of 16 mm or more, to withstand the high pressure inside the pipe section 10.

In front of the window 11 an image capturing device 20 is positioned. The image capturing device 20 may be a digital camera. The image capturing device 20 is orientated such that it can capture an image of the mixture through the window 11. The image capturing device 20 comprises a lens directed to the window 11. The distance between the lens and the window may be less than 3 cm.

The image capturing device 20 may be capable of capturing an image which has less than 100 µm movement blur, preferably even less than 50 µm this may for instance be achieved by an image capturing device which can capture an image with a shutter time of 0,00001s or less. In order to improve the sharpness of the image, the image capturing device 20 may capture images in black and white. The focusing area of the image capturing device may be in the range of 1-5 mm behind the window.

A light source 21 is provided and orientated such that light generated by the light source enter the pipe section 10 through the window 11. Preferably, the light source 21 is positioned such that light reflected by the window 11 does not fall upon the lens of the image capturing device 20.

In order to get an even light distribution the light source 21 may be provided by a ring-shaped light source 21 positioned around the image capturing device 20 or at least positioned concentrically with respect to a viewing line or viewing direction of the image capturing device. This ensures that the light is distributed evenly.

The measurement device 1 further comprises or is controlled by a control unit 22. The control unit 22 may be arranged as a computer device, comprising memory 22.2 and a processor 22.1. The control unit 22 may comprise an input/output device 22.3 to allow the control unit 22 to communicate with remote devices, such as the image capturing device 20, the light source 21 and for instance with a (collecting or discharge) pump 30,60 (which will be described below).

The collecting pump 30 is used in the process of collecting material from an underwater bottom. The control unit 22 may also be arranged to communicate with a discharge pump 60, or with equipment used in collecting material (dredging equipment, mining equipment) or discharging collected material.

The memory 22.2 may be arranged to store data and programming lines. The processor 22.1 may be arranged to read and execute the programming lines to provide the measurement device 1 with the functionality according to the embodiments described here. Captured image may be stored in the memory 22.2. Captured image may be read from the memory 22.2 by the processor 22.1 for further analysis. The programming lines may provide the control unit 22 with the functionality to analyse the captured image and determine information about a grain size distribution of the collected material from the captured image, e.g. using image recognition techniques.

The information about the grain size distribution may be processed into a grain size distribution of the collected material.

The determined information about the grain sizes and the grain size distribution(s) may be stored in the memory 22.2.

Figure 3:
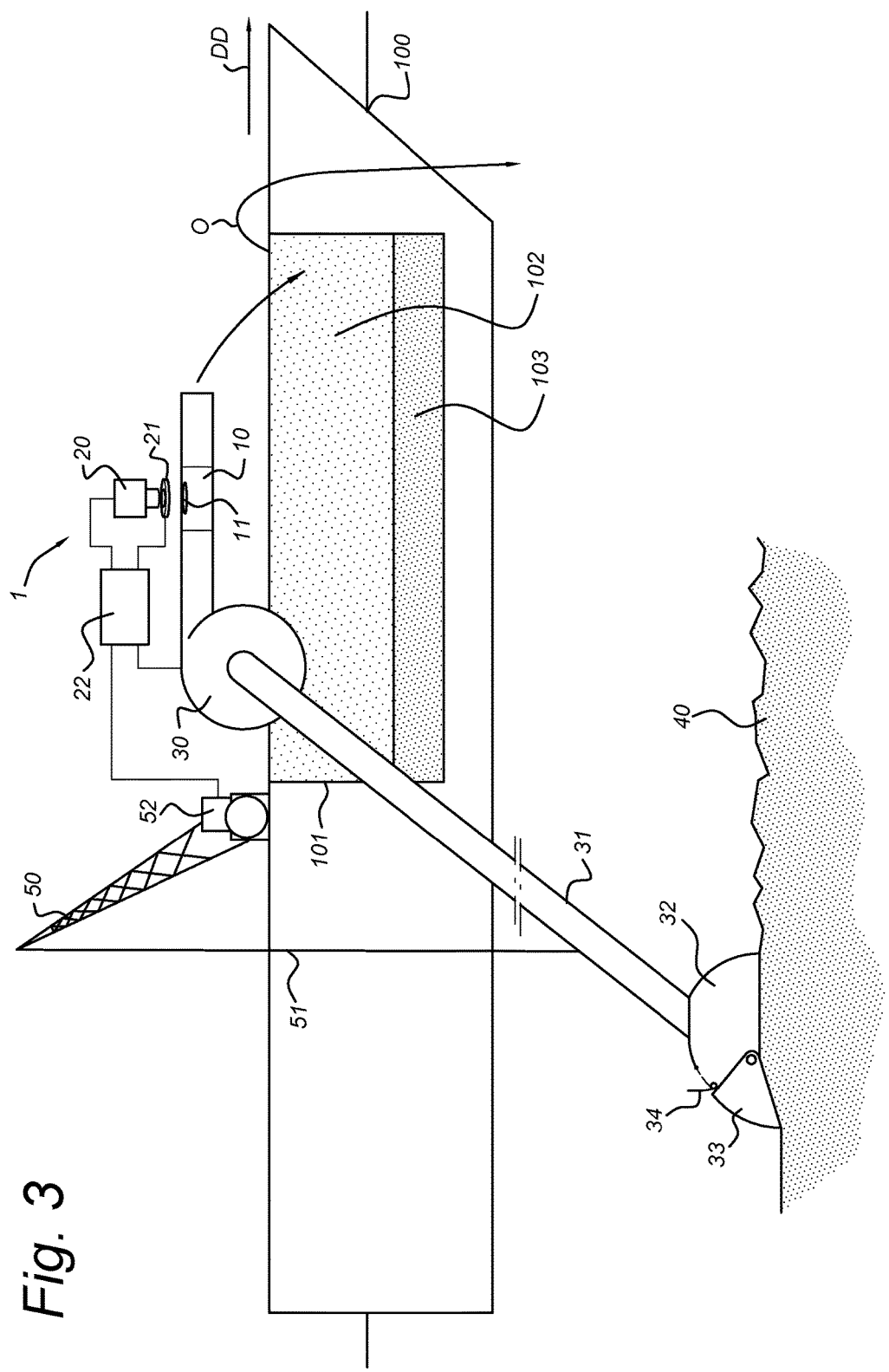

FIG. 3 schematically shows a dredging vessel 100 comprising a loading space 101.

The dredging vessel 100 comprises a measurement device 1 as described above. The dredging vessel 100 comprises a collecting pipe 31 arranged to transport a mixture of dredged material and water into the loading space 101 using a collecting pump 30. Part of the collecting pipe 31 is movably attached to the dredging vessel 100. The collecting pipe 31 can be lowered to a position wherein its free end is at an underwater position to rest on an underwater floor 40 (as shown in FIG. 3) and can be lifted to store the free end of the collecting pipe 31 above water, for instance on the deck of the dredging vessel 100. Lowering and lifting may be done with one or more hoisting devices 50, such as a crane 50 with a hoisting rope 51 and a hoisting winch 52. The free end of the collecting pipe 31 comprises a drag head 32. The drag head may for instance comprise a visor 33 and/or a water flap 34. The visor 33 is provided at a trailing end of the drag head 32 and rotatable about an axis which is substantial horizontal and perpendicular to a dredging direction to set a dredging depth. The water flap 34 may be provided to open or close an opening in drag head 34 to regulate the inflow of water into the drag head 32. The water flap may span the width of the drag head 32. The visor 33 and the water flap 34 may be controllable by the control unit 22.

The drag head 32 may further comprise jets to provide additional water to the inside of the drag head 32 and to improve the loosening of material from the underwater bottom 40.

FIG. 3 further shows that the loading space 101 is filled with the mixture of water and dredged material. In the loading space 101 a settled bed 103 is formed at the bottom of the loading space 101. Above the settled bed 103 is a mixture soup 102, i.e. a mixture of water and unsettled dredged material. Further shown is that part of the mixture soup 102 leaves the loading space 101 via overflow O (depicted schematically).

It will be understood that the description of FIG. 3 will also apply to a mining vessel. Instead of a drag head, a mining tool would then be provided at the free end of the collecting pipe 31.

Next, the functioning of the embodiments will be described. First the dredging vessel is prepared for dredging. The drag head 32 is lowered and positioned on the underwater floor 40. The visor 33 and the water flap 34 are set in a starting position.

The dredging vessel 100 is moved in a dredging direction DD and the drag head 32 loosens material from the underwater bottom and mixes it with water creating an mixture of water and collected material, in this example dredged material.

Collecting pump 30 is operated to pump the mixture through the collecting pipe 31 and also through the pipe section 10 part of the measurement device 1.

Figure 2:
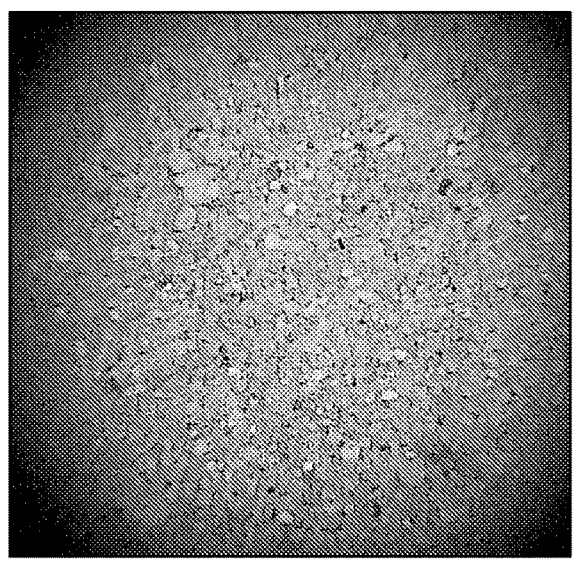
FIG. 2 shows an image captured by a measurement device according to an embodiment, FIG. 3 schematically shows a collecting vessel according to an embodiment, and FIG. 4 schematically shows a collecting vessel according to an other embodiment.

The control unit 22 controls the image capturing device 20 to capture at least one image of the mixture through window 11. An example of such a captured image is shown in FIG. 2.

The control unit 22 then processes the captured image using appropriate image processing techniques to determine information about the sizes of the grains present in the image. Of course, the control unit 22 may combine information from a plurality of images to determine information about the sizes of the grains present in the image.

Based on the information obtained, which can be an average grain size or a grain size distribution (such as provided in the table above), the dredging process can be controlled, in particular, the ratio of water and dredged material can be altered to optimize the dredging process by reducing losses via the overflow O. Controlling the ratio of water and dredged material in the mixture can be done by the control unit 20 by generating and emitting control signals via input/output device 22.3 to
 the collecting pump 30 to control a rotational speed of the pump 30,
 the visor 33 to control a position of the visor 33 provided on a drag head, and
 controlling a water flap provided on the drag head and/or controlling the hoisting device 50.

If the level in the loading space 101 hasn't reached the overflow level O the ratio between water and dredged material may be controlled as if the overflow has been reached. When the averaged grain size is large then more water with higher mixture speed can be used to increase the production, because the grains settles fast and the excess of water can be put easily overboard as soon as the mixture level reaches the overflows.

However when the average grain size is so small that the grain hardly settles, than less water has to be used, so that the mixture level reaches the overflow level later. If more water would be used, then the overflow level O would be reached earlier and overflowing would start earlier with putting more fine soil overboard then when using less water. Using too much water will thus result in larger overflow losses (which is bad for the surrounding) and requires more time to load the loading space.

For instance the measurement device can also be used for pumping mixture to shore via a discharge pipe line. The measurement device 1 or the control unit 22 can then calculate the critical velocity based on the average grain size or grain size distribution, to prevent settling of grains in the discharge pipe line with the risk of blocking the discharge pipeline.

On another embodiment relating to dredging may comprise providing a collecting pipe on a so called ladder which is with one end connected to a collecting pump for pumping the mixture and which collecting pipe is at its free end provided with a cutter head. The cutter head is positioned at the underwater bottom. The ladder—and so the cutter head—may comprise controllable members, such as a water valve to regulate the amount of water being pumped and winches. The winches may be provided at the end of the ladder and can be controlled in depth and swing speed (using swing winches) and so regulating the ratio of water and dredged material being pumped through the collecting pipe.

It will be understood that the above explanation of a dredging process may be applied mutatis mutandis to a mining vessel.

Figure 4:
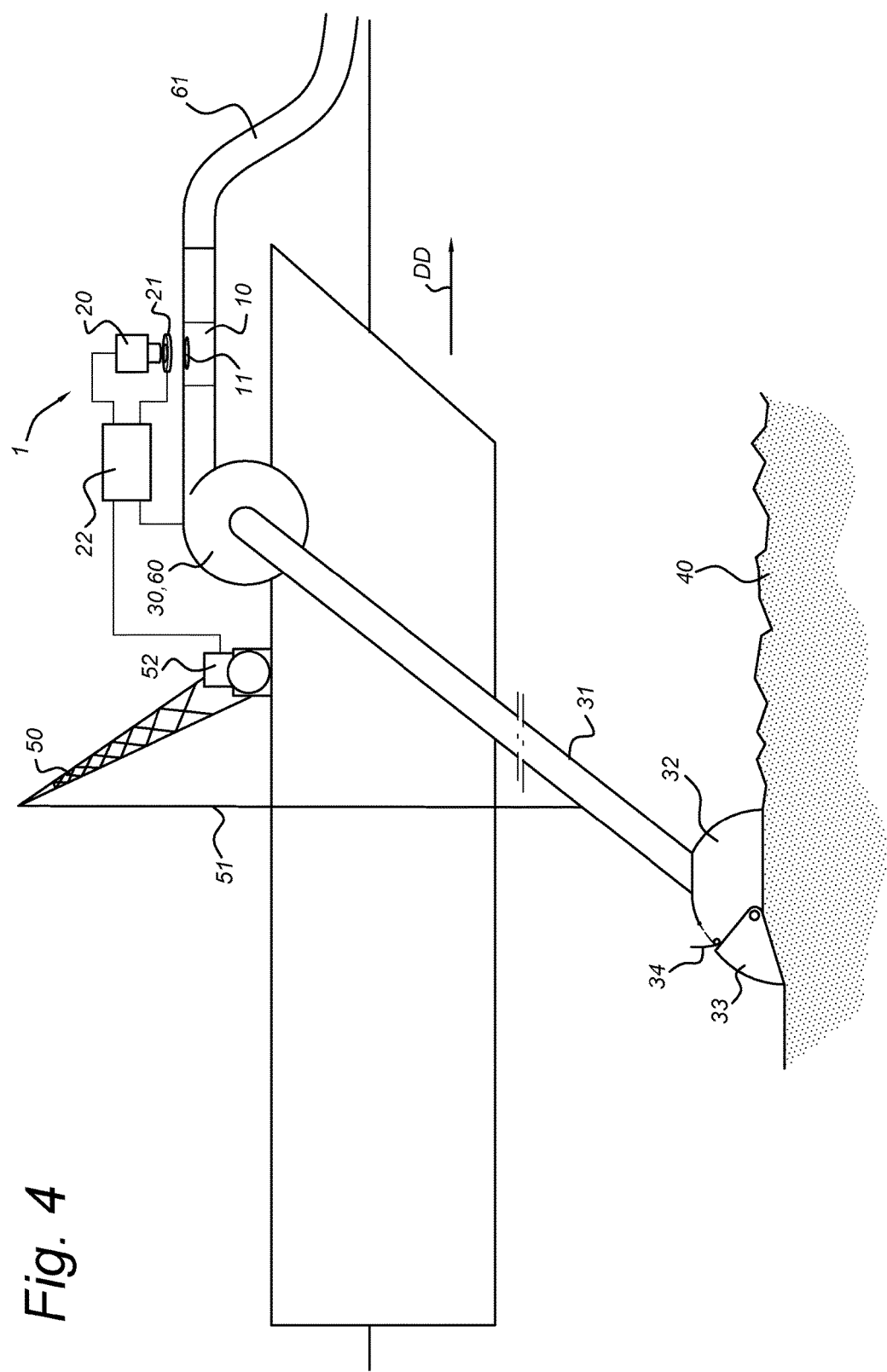

FIG. 4 shows an alternative embodiment, wherein a mixture is discharged via a discharge pump 60. The mixture may be discharged directly when collected from the underwater bottom (as shown in FIG. 4), in which case the collecting and discharge pump 30, 60 may be one and the same. The mixture may also be discharged from a loading space (not shown in FIG. 4).

By controlling the rotational speed (revolutions per minute) of the collecting and/or discharge pump 30, 60, the ratio of water and dredged material can be controlled. A lower rotational speed results in less water (with respect to dredged material), resulting in a higher density of the mixture. A higher rotational speed results in more water (with respect to dredged material), resulting in a lower density of the mixture.

If fine material is dredged (e.g. on a trailing suction hopper dredger) then one has to use as little water as possible, so one has to increase the density by reducing the mixture transport velocity (by reducing the pump speed) and/or by reducing the water gaps around the drag head which excavates the soil from the bottom, e.g. by closing water flaps.

For coarser material one can increase the mixture velocity by increasing the pump speed and/or the water gaps of the drag head, e.g. by opening water flaps. This increases the production and the surplus of transport water, but this is not a problem, because this can easily put overboard without too much soil, because this coarser soil settles down fast. With fine material a surplus of water takes also fine material overboard which decreases the production. For each grain size distribution there is an optimal transport velocity: a lower or higher velocity results in a smaller (than maximum) production.

For discharging a mixture the critical velocity has to be calculated from the measurement to prevent settling of the mixture in the discharge pipe line. Mixture speeds below the critical velocity will result in settling of grains with the risk of blocking of the discharge pipeline. If the calculation is based on the average grain size the critical velocity may be calculated too low, in particular when the distribution around the average is larger than expected. In that case the discharge speed may be set too low, resulting in the settling of large grains. So the amount of large grains influences the critical mixture velocity.

It will be clear that the embodiments described above are described only by way of example and not in any limiting sense, and that different modifications and adaptations are possible without exceeding the scope of the invention, and that the scope is determined only by the attached claims.

The invention claimed is:

1. A measurement device for performing measurements on a mixture of water and material collected from a mining or dredging operation using a vessel, the measurement device comprising:
    a collecting pipe comprising a straight pipe section through which the mixture can be guided, the pipe section comprising a window,
    a collecting pump connected to the collecting pipe;
    the collecting pipe further comprising a free end comprising a drag head and an end movably connected to the vessel, wherein the free end can be lowered to an underwater position,
    an image capturing device arranged to capture an image of the collected material through the window, and
    a density measurement device for measuring the density of the water and collected materials in the straight pipe section.

2. The measurement device according to claim 1, wherein the measurement device further comprises a control unit arranged to receive the image captured by the image capturing device and analyze the image to determine information about the collected material, including at least one of an average grain size and a grain size distribution of the collected material.

3. The measurement device according to claim 2, wherein the control unit is arranged to analyze the image to determine information about at least one of the average grain size and the grain size distribution of the collected material using image recognition techniques.

4. The measurement device according to claim 1, and further comprising a light source, arranged to generate a light beam to light at least part of the slurry in the image of the image capturing device.

5. The measurement device according to claim 4, wherein the light source is a ring-shaped light source positioned concentrically with respect to a viewing direction of the image capturing device.

6. The measurement device according to claim 1, wherein the image capturing device is arranged to capture an image which has a movement blur of less than 100 μm.

7. The measurement device according to claim 6, wherein the image capturing device is arranged to capture an image with a shutter time of 0.00001s or less.

8. The measurement device according to claim 1, wherein the window is arranged to withstand a pressure difference of 30 bar, between an inside of the pipe section and an outside of the pipe section.

9. The measurement device according to claim 1, wherein the image capture device is arranged to capture images in black and white.

10. The measurement device according to claim 1, wherein the image capturing device is set to capture an image with a focusing area positioned at a distance behind the window, the distance being in the range of 1-5 mm.

11. The measurement device according to claim 1, wherein the control unit is arranged to generate control signals to control at least one of a pump, a visor, a water flap, a hoisting device, a water valve and swing winches based on one or more captured images of the collected material.

12. A vessel for collecting material from an underwater bottom during a mining or dredging operation, the vessel comprising:
    a collecting pipe which has a first end movably connected to the vessel and a free end, which free end can be lowered to an underwater position, the collecting pipe comprising a straight pipe section that includes a window, a collecting device located at a free end of the collecting pipe, a collecting pump used in the process of collecting material from underwater bottom, a first measurement device comprising a first image capturing device arranged to capture an image of the collected material through the window and a density measurement device for measuring a density of the mixture the density of the water and collected materials in the straight pipe section.

13. The vessel according to claim 12, wherein the vessel comprises:

a discharge pump for discharging the collected material via a discharge pipe line, the discharge pipe line comprising a discharge pipe section, the discharge pipe section comprising a discharge pipe section window, and a second measurement device second image capturing device arranged to capture an image of the collected material through the discharge pipe section window.

14. The vessel according to claim 12, wherein the vessel further comprises a control unit arranged to receive and analyze at least one image captured by the first image capturing device and generate control signals to control at least one of a collecting pump, a discharge pump, a visor, a water flap, a hoisting device, a water valve and one or more swing winches in dependence on the at least one captured image.

15. A method of transporting a mixture of water and collected material, wherein the method is part of a dredging or mining process, and wherein the method comprises:

collecting material from an underwater bottom or from loading space by loosening material from the underwater bottom or from the loading space with a drag head at a free end of a collecting pipe, the other end of the collecting pipe being movably connected to a vessel, mixing the material with water creating the mixture of water and collected material, operating a collecting pump to pump the mixture through the collecting pipe to the vessel, capturing at least one image of the collected material flowing through the pipe and analyzing the at least one image, measuring the density of the mixture of water and collected materials in a straight pipe section, and controlling at least one of a ratio of water and collected material in the mixture and an operating speed of the pump based on the captured image and the measured density.

16. The method according to claim 15, wherein controlling the ratio of water and collected material in the mixture is done by one or more of:

controlling a rotational speed of the collecting pump, controlling a position of a visor provided on the drag head of a trailing suction hopper dredger, controlling a water flap provided on the drag head of a trailing suction hopper dredger, controlling a depth of the excavation tool by a hoisting device, controlling a water valve provided on the collecting pipe of a cutter dredger, and controlling a swing speed of a cutter dredger by swing winches.

17. The vessel of claim 14, wherein the control unit generates control signals to control at least one of a collecting pump, a discharge pump, a visor, a water flap, a hoisting device, a water valve and one or more swing winches based on determined information about at least one of an average grain size and a grain size distribution of the collected material.

* * * * *